US008834912B2

(12) United States Patent
Atanasoska et al.

(10) Patent No.: US 8,834,912 B2
(45) Date of Patent: Sep. 16, 2014

(54) MEDICAL DEVICES HAVING MULTIPLE CHARGED LAYERS

(75) Inventors: Liliana Atanasoska, Edina, MN (US); Jan Weber, Maple Grove, MN (US); James Lee Shippy, III, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2070 days.

(21) Appl. No.: 11/322,905

(22) Filed: Dec. 30, 2005

(65) Prior Publication Data
US 2007/0154513 A1 Jul. 5, 2007

(51) Int. Cl.
*A61F 2/915* (2013.01)
*A61F 2/91* (2013.01)
*A61L 27/28* (2006.01)
*A61L 27/54* (2006.01)
*A61L 15/46* (2006.01)
*A61L 31/08* (2006.01)
*A61L 31/16* (2006.01)
*A61F 2/00* (2006.01)

(52) U.S. Cl.
CPC ............ *A61L 15/46* (2013.01); *A61F 2/915* (2013.01); *A61L 2420/04* (2013.01); *A61F 2/91* (2013.01); *A61F 2310/00592* (2013.01); *A61F 2/0077* (2013.01); *A61L 27/28* (2013.01); *A61F 2310/0097* (2013.01); *A61F 2002/91533* (2013.01); *A61F 2002/91575* (2013.01); *A61F 2310/00574* (2013.01); *A61L 27/54* (2013.01); *A61L 2300/61* (2013.01); *A61L 2400/12* (2013.01); *A61L 31/08* (2013.01); *A61L 31/16* (2013.01); *A61F 2002/91525* (2013.01)
USPC .......................................................... 424/423

(58) Field of Classification Search
None
See application file for complete search history.

(56) References Cited

U.S. PATENT DOCUMENTS

| | | | | |
|---|---|---|---|---|
| 5,208,111 | A | 5/1993 | Decher et al. .................. | 428/420 |
| 5,468,574 | A | 11/1995 | Ehrenberg et al. .............. | 429/33 |
| 5,614,549 | A | 3/1997 | Greenwald et al. ........... | 514/449 |
| 5,733,925 | A | 3/1998 | Kunz et al. ...................... | 514/449 |
| 5,840,387 | A | 11/1998 | Berlowitz-Tarrant et al. ............. | 428/36.91 |
| 5,849,415 | A * | 12/1998 | Shalaby et al. ................ | 428/419 |
| 5,871,554 | A * | 2/1999 | Patil et al. ........................ | 44/331 |
| 5,977,163 | A | 11/1999 | Li et al. .......................... | 514/449 |
| 6,020,175 | A | 2/2000 | Onda et al. ..................... | 435/180 |
| 6,545,097 | B2 | 4/2003 | Pinchuk et al. ............... | 525/240 |
| 6,669,980 | B2 | 12/2003 | Hansen ......................... | 427/2.24 |
| 6,730,349 | B2 | 5/2004 | Schwarz et al. ............... | 427/2.1 |
| 6,730,699 | B2 | 5/2004 | Li et al. .......................... | 514/449 |
| 6,764,709 | B2 | 7/2004 | Flanagan ....................... | 427/2.1 |
| 6,827,966 | B2 | 12/2004 | Qiu et al. ...................... | 427/2.24 |
| 2002/0032434 | A1* | 3/2002 | Chudzik et al. ............ | 604/890.1 |
| 2002/0037383 | A1 | 3/2002 | Spillman, Jr. et al. | |
| 2002/0061326 | A1 | 5/2002 | Li et al. ......................... | 424/424 |
| 2002/0127327 | A1 | 9/2002 | Schwarz et al. | |
| 2002/0128234 | A1* | 9/2002 | Hubbell et al. ............... | 514/100 |
| 2002/0143382 | A1 | 10/2002 | Hijlkema et al. | |
| 2003/0054090 | A1 | 3/2003 | Hansen | |
| 2003/0087024 | A1 | 5/2003 | Flanagan | |
| 2003/0087111 | A1* | 5/2003 | Hubbell et al. ............... | 428/457 |
| 2003/0124368 | A1 | 7/2003 | Lynn et al. | |
| 2003/0139795 | A1 | 7/2003 | Olson | |
| 2003/0139798 | A1 | 7/2003 | Brown et al. | |
| 2003/0139806 | A1 | 7/2003 | Haverkost et al. | |
| 2003/0143315 | A1 | 7/2003 | Pui et al. | |
| 2003/0157260 | A1 | 8/2003 | Rubner et al. | |
| 2003/0166507 | A1* | 9/2003 | Li et al. ............................. | 514/2 |
| 2003/0211129 | A1* | 11/2003 | Spillman et al. .............. | 424/423 |
| 2003/0235603 | A1 | 12/2003 | Schwarz et al. | |
| 2003/0236323 | A1 | 12/2003 | Ratner et al. ..................... | 524/27 |
| 2004/0013721 | A1 | 1/2004 | Antipov et al. | |
| 2004/0022824 | A1 | 2/2004 | Li et al. | |
| 2004/0033364 | A1 | 2/2004 | Spiridigliozzi et al. | |
| 2004/0059409 | A1 | 3/2004 | Stenzel | |
| 2004/0081745 | A1 | 4/2004 | Hansen | |
| 2004/0106841 | A1 | 6/2004 | Shaw et al. | |
| 2004/0106987 | A1 | 6/2004 | Palasis et al. | |
| 2004/0133271 | A1 | 7/2004 | Jang | |
| 2004/0142910 | A1 | 7/2004 | Vachon et al. | |
| 2004/0172121 | A1 | 9/2004 | Eidenschink et al. | |
| 2004/0182511 | A1 | 9/2004 | Rakos et al. | |
| 2004/0185168 | A1 | 9/2004 | Weber et al. | |
| 2004/0202691 | A1 | 10/2004 | Richard | |
| 2004/0230298 | A1 | 11/2004 | Udipi et al. | |

(Continued)

FOREIGN PATENT DOCUMENTS

WO    WO 2004/112863 A1    12/2004    ............ A61L 31/10

OTHER PUBLICATIONS

Scheller et al., Acute cardiac tolernce of current contrast media and the new taxane protaxel using iopromide as carrier during porcine coronary angiography and stenting, Investigative Radiology, 2002, vol. 37, pp. 29-34.*

Kolodgie et al., Sustained reduction of in-stent neointimal growth with the use of a novel systemic nanoparticle paclitaxel, Circulation, 2002, vol. 106, pp. 1195-1198.*

Jad A. Jaber et al., "Polyelectrolyte Multilayers with Reversible Thermal Responsivity", Macromolecules, 2005, vol. 38, pp. 1300-1306.

(Continued)

*Primary Examiner* — Kevin S Orwig
*Assistant Examiner* — Ping Cao
(74) *Attorney, Agent, or Firm* — Fish & Richardson P.C.

(57) ABSTRACT

According to an aspect of the present invention, medical devices are provided, which are adapted for implantation or insertion into a subject and which include at least one multi-layer region that contains multiple charged layers of alternating charge. The multiple charged layers, in turn, include the following: (i) at least one charged block copolymer (e.g., a charged block copolymer that contains one or more polyelectrolyte blocks) and (ii) at least one charged therapeutic agent (e.g., a charged therapeutic agent that contains one or more polyelectrolyte blocks).

28 Claims, 1 Drawing Sheet

(56) References Cited

U.S. PATENT DOCUMENTS

| | | |
|---|---|---|
| 2004/0241202 A1 | 12/2004 | Chluba et al. |
| 2004/0249469 A1 | 12/2004 | Cohen et al. ............... 623/23.6 |
| 2005/0002865 A1 | 1/2005 | Klaveness et al. ........... 424/9.52 |
| 2005/0013872 A1 | 1/2005 | Freyman |
| 2005/0025801 A1 | 2/2005 | Richard et al. |
| 2005/0025802 A1 | 2/2005 | Richard et al. |
| 2005/0025803 A1 | 2/2005 | Richard et al. |
| 2005/0027283 A1 | 2/2005 | Richard et al. |
| 2005/0033407 A1 | 2/2005 | Weber et al. |
| 2005/0037047 A1 | 2/2005 | Song |
| 2005/0037048 A1 | 2/2005 | Song |
| 2005/0037050 A1 | 2/2005 | Weber ........................... 424/426 |
| 2005/0112172 A1* | 5/2005 | Pacetti ........................... 424/423 |
| 2005/0129727 A1 | 6/2005 | Weber et al. .................. 424/423 |
| 2005/0208100 A1 | 9/2005 | Weber et al. .................. 424/426 |
| 2006/0184092 A1 | 8/2006 | Atanasoska et al. |

OTHER PUBLICATIONS

Elvira Tjipto et al., "Assembly of Multilayer Films from Polyelectrolytes Containing Weak and Strong Acid Moieties", Langmuir, 2005, vol. 21, pp. 8785-8792.

Hua Ai et al., "Applications of the Electrostatic Layer-by-Layer Self-Assembly Technique in Biomedical Engineering," Proceedings of the Second Joint EMBS/BMES Conference, Houston, Oct. 23-26, 2002, pp. 502-503.

Shrirang V. Ranade et al., "Physical characterization of controlled release of paclitaxel from the TAXUS™ Express²™ drug-eluting stent," *Journal of Biomedical Materials Research Part A*, vol. 71A(4), 2004, pp. 625-634.

Kris C. Wood et al., "Tunable Drug Release from Hydrolytically Degradable Layer-by-Layer Thin Films," *Langmuir*, vol. 21, 2005, pp. 1603-1609.

Benjamin Thierry et al., "Delivery Platform for Hydrophobic Drugs: Prodrug Approach Combined with Self-Assembled Multilayers," *Journal of the American Chemical Society*, vol. 127, 2005, pp. 1626-1627.

Benjamin Thierry et al., "Bioactive Coatings of Endovascular Stents Based on Polyelectrolyte Multilayers," *Biomacromolecules*, vol. 4, 2003, pp. 1564-1571.

D.G. Kurth et al., "Multilayers on Solid Planar Substrates: From Structure to Function," in *Multilayer Thin Films—Sequential Assembly of Nanocomposite Materials*, G. Decher, J.B. Schlenoff, eds., Wiley-VCH, Weinheim 2002, pp. 393-426.

Eric W.P. Damen et al., "Paclitaxel Esters of Malic Acid as Prodrugs with Improved Water Solubility," *Bioorganic & Medicinal Chemistry*, vol. 8, 2000, pp. 427-432.

Mi-Kyoung Park et al., "Self-Assembly and Characterization of Polyaniline and Sulfonated Polystyrene Multilayer-Coated Colloidal Particles and Hollow Shells," *Langmuir*, vol. 19, 2003, pp. 8550-8554.

Chun Li, "Poly(L-glutamic acid)-anticancer drug conjugates," *Advanced Drug Delivery Reviews*, vol. 54, 2002, pp. 695-713.

Ruth Duncan, "Polymer conjugates for tumour targeting and intracytoplasmic delivery. The EPR effect as a common gateway?" PSTT, vol. 2, 1999, pp. 441-449.

C.A. Edmondson et al., "Free volume and percolation in S-SEBS and fluorocarbon proton conducting membranes," *Solid State Ionics*, vol. 152-153, 2002, pp. 355-361.

Winky Hau et al., "Surface-chemistry technology for microfluidics," *J. Micromech. Microeng.*, vol. 13, 2003, pp. 272-278.

R. Duncan et al., "Polymer-drug conjugates, PDEPT and PELT: basic principles for design and transfer from the laboratory to clinic," *Journal of Controlled Release*, vol. 74, 2001, pp. 135-146.

W. Tansey et al., "Synthesis and characterization of branched poly(L-glutamic acid) as a biodegradable drug carrier," *Journal of Controlled Release*, vol. 94, 2004, pp. 39-51.

R.I. Blackwell et al., "Dynamic mechanical properties of annealed sulfonated poly(styrene-b-[ethylene/butylenes]-b-styrene) block copolymers," *Polymer*, vol. 45, 2004, pp. 3457-3463.

Prince Antony et al., "Atomic force microscopic studies of novel arborescent block and linear triblock polystyrene-polyisobutylene copolymers," *European Polymer Journal*, vol. 40, 2004, pp. 149-157.

Igor L. Radtchenko et al., "A novel method for encapsulation of poorly water-soluble drugs: precipitation in polyelectrolyte multilayer shells," *International Journal of Pharmaceutics*, vol. 242, 2002, pp. 219-223.

"Functionalization of Polymer Surfaces," Europlasma Technical Paper, May 8, 2004, 29 pgs.

Ivan Yu. Sakharov et al., "Modeling and characterization of polyelectrolyte complex of polyaniline and sulfonated polystyrene produced by palm tree peroxidase," *Synthetic Metals*, vol. 142, 2004, pp. 127-135.

Srivatsan Kidambi et al., "Selective Depositions on Polyelectrolyte Multilayers: Self-Assembled Monolayers of m-dPEG Acid as Molecular Template," *Journal of the American Chemical Society*, vol. 126, 2004, pp. 4697-4703.

Jaber G. Qasem et al., "Kinetics of Paclitaxel 2'-N-methylpyridinium Mesylate Decomposition," *AAPS PharmSciTech2003*, vol. 4(2), Article 21, 8 pgs.

Wenguang Liu et al., "An investigation on the physiochemical properties of chitosan/DNA polyelectrolyte complexes," *Biomaterials*, vol. 26, 2005, pp. 2705-2711.

Yossef A. Elabd et al., "Triblock copolymer ionomer membranes Part I. Methanol and proton transport," *Journal of Membrane Science*, vol. 217, 2003, pp. 227-242.

Yossef A. Elabd et al., "Sulfonation and characterization of poly(styrene-isobutylene-styrene) triblock copolymers at high ion-exchange capacities," *Polymer*, vol. 45, 2004, pp. 3037-3043.

J.E. Puskas et al., "The effect of hard and soft segment composition and molecular architecture on the morphology and mechanical properties of polystyrene-polyisobutylene thermoplastic elastomeric block copolymers," *European Polymer Journal*, vol. 39, 2003, pp. 2041-2049.

R.F. Storey et al., "Poly(styrene-*b*-isobutylene-*b*-styrene) block copolymers produced by living cationic polymerization. Part III. Dynamic mechanical and tensile properties of block copolymers and ionomers therefrom," *Polymer*, vol. 42, 2001, pp. 2321-2330.

Ruth Duncan, "The Dawning Era of Polymer Therapeutics," *Nature Reviews/Drug Discovery*, vol. 2, 2003, pp. 347-360.

Yongmoon Kwon et al., "Investigation of the effect of reaction conditions on the synthesis of multiarm-star polyisobutylene-polystyrene block copolymers," *European Polymer Journal*, vol. 40, 2004, 119-127.

J. Kopecek et al., "Water soluble polymers in tumor targeted delivery," *Journal of Controlled Release*, vol. 74, 2001, pp. 147-158.

* cited by examiner

MEDICAL DEVICES HAVING MULTIPLE CHARGED LAYERS

FIELD OF THE INVENTION

The present invention relates to implantable and insertable medical devices having multiple charged layers.

BACKGROUND

Various medical devices have been developed.

Specific examples of such devices include drug eluting coronary stents, which are commercially available from Boston Scientific Corp. (TAXUS®), Johnson & Johnson (CYPHER®), and others. These existing products are based on metallic balloon expandable stents with biostable polymer coatings, which release antiproliferative drugs at a controlled rate and total dose.

Specific examples of polymers for drug eluting polymer coatings include block copolymers, such as block copolymers containing polyisobutylene and polystyrene blocks, for instance, polystyrene-polyisobutylene-polystyrene triblock copolymers (SIBS copolymers), which are described in U.S. Pat. No. 6,545,097 to Pinchuk et al. These polymers have proven valuable in implantable and insertable medical devices for a variety of reasons, including their excellent elasticity, strength and biocompatibility. Moreover, they have proven to be effective drug delivery systems for providing therapeutic agents to sites in vivo.

These and other polymers, however, are typically applied to underlying substrates via spray coating processes, which have a number of less than desirable characteristics including the following, among others: (a) spraying processes typically require a line-of-sight trajectory between the spray source and the surface to be coated, meaning that complete coverage may not be achieved for a variety of substrates, (b) material losses are commonly high for spraying processes, with significant portions of the spray stream not being deposited on the substrate, particularly for substrates which have a significant amount of void space, such as cardiovascular stents, and (c) where a drug is included in the spray coating, it is very difficult to achieve a homogeneous dose distributions over underlying substrate.

SUMMARY OF THE INVENTION

In accordance with certain aspects of the present invention, medical devices are provided which are configured for implantation or insertion into a subject. The medical devices include at least one multilayer region that contains multiple charged layers of alternating charge. The multiple charged layers, in turn, include the following: (i) at least one charged polymer (e.g., a charged block copolymer that contains one or more polyelectrolyte blocks) and (ii) at least one charged therapeutic agent (e.g., a charged therapeutic agent that contains one or more polyelectrolyte blocks).

According to certain other aspects of the present invention, methods are provided for making such medical devices. These methods include applying a series of charged layers over a substrate, wherein each successive layer in the series is opposite in charge relative to the previously applied layer.

Advantages of the present invention include one or more of the following, among others: (a) the ability to provide coverage of substrate surfaces that are hidden from view (e.g., surfaces which cannot be reached by a line-of-sight trajectory, such as a spray trajectory), (b) the ability to fill the pores of porous substrates, (c) low material losses, due to the self assembling nature of such layers, (d) excellent thickness and uniformity control, (e) the ability to process large batches of devices, (f) good substrate adhesion, (g) where a drug is present, the ability to readily provide homogeneous dose distributions across the substrate surfaces, and (h) the ability to tailor the polymer-drug architecture (e.g., the ability to accurately position the location of the drug within the coating).

These and other aspects, embodiments and potential advantages of the present invention will become immediately apparent to those of ordinary skill in the art upon reading the Detailed Description to follow.

DETAILED DESCRIPTION

Figure 1A:
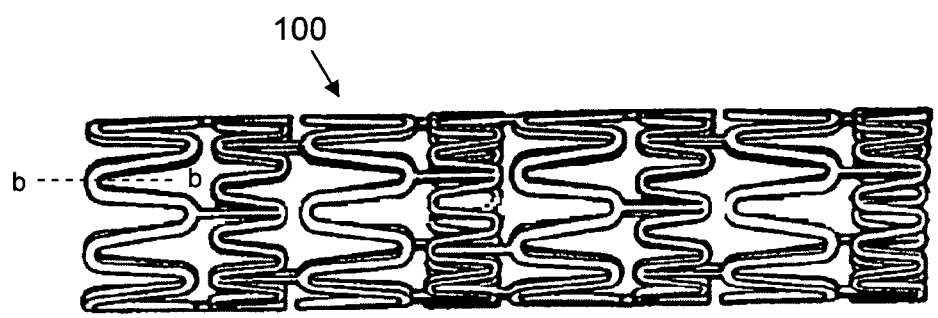
FIG. 1A is a schematic view of a stent in accordance with an embodiment of the present invention.

According to one aspect of the present invention, medical devices are provided, which are adapted for implantation or insertion into a subject, and which include at least one multilayer region that contains multiple charged layers of alternating charge. The multiple charged layers, in turn, include the following: (i) at least one charged polymer (e.g., a charged copolymer, such as a charged block copolymer that contains one or more polyelectrolyte blocks) and (ii) at least one charged therapeutic agent (e.g., a therapeutic agent that contains one or more polyelectrolyte blocks).

As used herein, "polymers" are molecules containing multiple copies (e.g., 5 to 10 to 25 to 50 to 100 to 250 to 500 to 1000 or more copies) of one or more constitutional units, commonly referred to as monomers.

Polymers may take on a number of configurations, which may be selected, for example, from cyclic, linear and branched configurations. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

Examples of implantable or insertable medical devices upon which multilayer regions may be applied include, for example, catheters (e.g., renal or vascular catheters including balloon catheters), guide wires, balloons, filters (e.g., vena cava filters), stents (including coronary vascular stents, peripheral vascular stents such as cerebral stents, urethral, ureteral, biliary, tracheal, gastrointestinal and esophageal stents), stent grafts, vascular grafts, vascular access ports, embolization devices including cerebral aneurysm filler coils (including Guglilmi detachable coils and metal coils), myocardial plugs, septal defect closure devices, patches, pacemakers and pacemaker leads, defibrillation leads and coils, heart valves, vascular valves, biopsy devices, patches for delivery of therapeutic agents, tissue engineering scaffolds for cartilage, bone, skin and other in vivo tissue regeneration, as well as other coated substrates (which can comprise, for example, glass, metal, polymer, ceramic and combinations thereof) that are implanted or inserted into the body.

The medical devices of the present invention include medical devices that are used for diagnostics, for systemic treatment, or for the localized treatment of any mammalian tissue or organ. Examples include tumors; organs including the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; dermal tissue; cartilage; and bone. As used herein, "treatment" refers to the prevention of a disease or condition, the reduction or elimination of symptoms associated with a disease or condition, or the substantial or complete elimination a disease or condition. Typical subjects are vertebrate subjects, more typically mammalian subjects including human subjects.

The multilayer region may be provided over all or only a portion of the substrate. The multilayer region may be provided in any shape or pattern (e.g., in the form of a series of rectangles, stripes, or any other continuous or non-continuous pattern). Techniques by which patterned multilayer regions may be provided are described below and include ink jet techniques, roll coating techniques, and so forth. Hence, multiple multilayer regions may be provided at different locations over the substrate surface. These regions may be the same as one another, or they may differ from one another, for example, on the basis of surface area, shape, number of layers, layer composition, and so forth.

The multilayer regions for the devices of the present invention may be assembled using layer-by-layer techniques. Layer-by-layer techniques may be used to coat a wide variety of substrate materials using charged materials via electrostatic self-assembly, which is generally understood to be based primarily on electrostatic interactions of oppositely charged ionic adsorbates. In a typical layer-by-layer technique, multilayer growth proceeds through sequential steps, in which the substrate is immersed in solutions of cationic and anionic species, frequently with intermittent rinsing between steps. In this way, a first layer having a first surface charge is typically deposited (or adsorbed) on an underlying substrate, followed by a second layer having a second surface charge that is opposite in sign to the surface charge of the first layer, and so forth. The charge on the outer layer is reversed upon deposition of each sequential layer.

Multilayer regions created using layer-by-layer self-assembly commonly include one or more types of polyelectrolytes as ionic species.

As used herein, "polyelectrolytes" are polymers having multiple (e.g., 5 to 10 to 25 to 50 to 100 to 250 to 500 to 1000 or more) charged groups (e.g., ionically dissociable groups that provide cations and anions).

Frequently, the number of charged groups is so large that the polymers are soluble in polar solvents (including water) when in ionically dissociated form (also called polyions). Depending on the type of dissociable groups, polyelectrolytes may be classified as polyacids and polybases. When dissociated, polyacids form polyanions, with protons being split off. Polyacids include inorganic, organic and bio-polymers. Examples of polyacids are polyphosphoric acids, polyvinylsulfuric acids, polyvinylsulfonic acids, polyvinylphosphonic acids and polyacrylic acids. Examples of the corresponding salts, which are also called polysalts, are polyphosphates, polyvinylsulfates, polyvinylsulfonates, polyvinylphosphonates and polyacrylates. Polybases contain groups which are capable of accepting protons, e.g., by reaction with acids, with a salt being formed. Examples of polybases having dissociable groups within their backbone and/or side groups are polyallylamine, polyethylimine, polyvinylamine and polyvinylpyridine. By accepting protons, polybases form polycations.

Some polyelectrolytes have both anionic and cationic groups, but nonetheless will have a net negative charge, for example, because the number of anionic groups outnumber the cationic groups, or will have a net positive charge, for example, because the number of cationic groups outnumber the anionic groups. In this regard, the net charge of a particular polyelectrolyte may change with the pH of its surrounding environment. Polyelectrolytes containing both cationic and anionic groups are categorized herein as either polycations or polyanions, depending on which groups predominate.

Thus, as defined herein, the term polyelectrolyte embraces a wide range of species, including polycations and their precursors (e.g., polybases, polysalts, etc.), polyanions and their precursors (e.g., polyacids, polysalts, etc.), polymers having multiple anionic and cationic groups (e.g., polymers having multiple acidic and basic groups such as a variety of proteins), ionomers (polyelectrolytes in which a small but significant proportion of the constitutional units carry charges), and so forth. Moreover, suitable polyelectrolytes include low-molecular weight polyelectrolytes (e.g., polyelectrolytes having molecular weights of a few hundred Daltons or less) up to macromolecular polyelectrolytes (e.g., polyelectrolytes of synthetic or biological origin, which commonly have molecular weights of several million Daltons or more).

Linear or branched polyelectrolytes may be used in some embodiments. Using branched polyelectrolytes can lead to less compact polyelectrolyte multilayers having a higher degree of wall porosity. Polyelectrolyte molecules may be crosslinked within or/and between the individual layers in some embodiments, e.g. by crosslinking amino groups with aldehydes, for example, to increase stability.

Specific examples of suitable polycations may be selected, for example, from the following: polyamines, including polyamidoamines, poly(amino methacrylates) including poly(dialkylaminoalkyl methacrylates) such as poly(dimethylaminoethyl methacrylate) and poly(diethylaminoethyl methacrylate), polyvinylamines, polyvinylpyridines including quaternary polyvinylpyridines such as poly(N-ethyl-4-vinylpyridine), poly(vinylbenzyltrimethylamines), polyallylamines such as poly(allylamine hydrochloride) (PAH) and poly(diallyldialklylamines) such as poly(diallyldimethylammonium chloride), spermine, spermidine, hexadimethrene bromide (polybrene), polyimines including polyalkyleneimines such as polyethyleneimines, polypropyleneimines and ethoxylated polyethyleneimines, basic peptides and proteins, including histone polypeptides and polymers containing lysine, arginine, ornithine and combinations thereof including poly-L-lysine, poly-D-lysine, poly-L,D-lysine, poly-L-arginine, poly-D-arginine, poly-D,L-arginine, poly-L-ornithine, poly-D-ornithine, poly-L,D-ornithine, gelatin, albumin, protamine and protamine sulfate, and polycationic polysaccharides such as cationic starch and chitosan, as well as copolymers, derivatives and combinations of the preceding, among various others.

Specific examples of suitable polyanions may be selected, for example, from the following: polysulfonates such as polyvinylsulfonates, poly(styrenesulfonates) such as poly(sodium styrenesulfonate) (PSS), sulfonated poly(tetrafluoroethylene), as well as sulfonated versions of various other homopolymers and copolymers, polysulfates such as polyvinylsulfates, sulfated and non-sulfated glycosaminoglycans as well as certain proteoglycans, for example, heparin, heparin sulfate, chondroitin sulfate, keratan sulfate, dermatan sulfate, polycarboxylates such as acrylic acid polymers and salts thereof (e.g., ammonium, potassium, sodium, etc.), for instance, those available from Atofina and Polysciences Inc., methacrylic acid polymers and salts thereof (e.g., EUDRAGIT®, a methacrylic acid and ethyl acrylate copolymer), carboxymethylcellulose, carboxymethylamylose and carboxylic acid derivatives of various other polymers, polyanionic peptides and proteins such as glutamic acid polymers and copolymers, aspartic acid polymers and copolymers, polymers and copolymers of uronic acids such as mannuronic acid, galatcuronic acid and guluronic acid, and their salts, for example, alginic acid and sodium alginate, hyaluronic acid, gelatin, and carrageenan, polyphosphates such as phosphoric acid derivatives of various polymers, polyphosphonates such as polyvinylphosphonates, polysulfates such as polyvinylsulfates, as well as copolymers, derivatives and combinations of the preceding, among various others.

Suitable substrates materials upon which the multilayer regions of the present invention may be formed may be selected from a wide variety of materials, including (a) organic materials (e.g., materials containing 50 wt % or more organic species) such as polymeric materials and (b) inorganic materials (e.g., materials containing 50 wt % or more inorganic species), such as metallic materials (e.g., metals and metal alloys) and non-metallic inorganic materials (e.g., carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon and carbon-based, ceramic-like materials such as carbon nitrides, among many others.

Specific examples of metallic inorganic materials may be selected, for example, from substantially pure metals (e.g., biostable metals such as gold, platinum, palladium, iridium, osmium, rhodium, titanium, tantalum, tungsten, and ruthenium, and bioresorbable metals such as magnesium and iron), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and bioabsorbable metal alloys such as magnesium alloys and iron alloys (including their combinations with Ce, Ca, Zn, Zr and Li), among many others.

Specific examples of organic materials include polymers (biostable or biodegradable) and other high molecular weight organic materials, which may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

Certain substrates are inherently charged and thus readily lend themselves to layer-by-layer assembly techniques.

To the extent that the substrate does not have an inherent net surface charge, a surface charge may nonetheless be provided. For example, where the substrate to be coated is conductive, a surface charge may be provided by applying an electrical potential to the same.

As another example, substrates, including polymeric substrates, may be chemically treated with various reagents, including reducing agents and oxidizing agents (e.g., sulfur trioxide for sulfonate formation), which modify their surfaces so as to provide them charged groups, such as such as amino, phosphate, sulfate, sulfonate, phosphonates and carboxylate groups, among many others.

Other techniques for providing surface charge include techniques whereby a surface region is treated with a reactive plasma. For example, gas discharge techniques have been used to functionalize polymer surfaces. Surface modification is obtained by exposing the surface to a partially ionized gas (i.e., to a plasma). Two types of processes are frequently described, depending on the operating pressure: corona discharge techniques (which are conducted at atmospheric pressure) and glow discharge techniques (which are conducted at reduced pressure). Because the plasma phase consists of a wide spectrum of reactive species (electrons, ions, etc.) these techniques have been used widely for functionalization of polymer surfaces.

Glow discharge techniques may be preferred over corona discharge techniques in certain embodiments, because the shape of the object to be treated is of minor importance during glow discharge processes. Moreover, glow discharge techniques are usually either operated in an etching or in a depositing mode, depending on the gas used, whereas corona discharge techniques are usually operated in an etching mode. A commonly employed glow discharge technique is radio-frequency glow discharge (RFGD).

Plasma treatment processes have been widely used to etch, crosslink and/or functionalize surfaces, with these processes occurring simultaneously at a surface that is exposed to a discharge of a non-polymerizable gas. The gas that is used primarily determines which of these processes is dominant. When gases like carbon monoxide (CO), carbon dioxide ($CO_2$), or oxygen ($O_2$) are used, functionalization with —COOH groups (which donate protons to form anionic groups) is commonly observed. When gases like ammonia, a propyl amine, or $N_2/H_2$ are employed, —$NH_2$ groups (which accept protons to form cationic groups) are commonly formed.

Functional group containing surfaces may also be obtained using plasma polymerization processes in which "monomers" are employed that contain functional groups. Allylamine (which produces —$NH_2$ groups) and acrylic acid (which produces —COOH groups) have been used for this purpose. By using a second feed gas (generally a non-polymerizable gas) in combination with the unsaturated monomer, it is possible to incorporate this second species in the plasma deposited layer. Examples of gas pairs include allylamine/$NH_3$ (which leads to enhanced production of —$NH_2$ groups) and acrylic acid/$CO_2$ (which leads to enhanced production of —COOH groups).

The above and further information on plasma processing may be found, for example, in "Functionalization of Polymer Surfaces," Europlasma Technical Paper, May 8, 2004 and in U.S. Patent Application Publication No. 2003/0236323.

Laser processes may be used to create surfaces having functionalized groups in any of a variety of patterns. A surface thus functionalized may then be used to create a patterned multilayer coating via layer-by-layer processes such as those discussed above. The functionalization processes may be based, for example, on essentially the same principles as the plasma-based techniques of the preceding paragraphs. However, by using laser radiation (in conjunction with the gas or gases), one may create a localized plasma in the vicinity of the laser beam (e.g., just above the focal point of the beam), leading to localized surface functionalization. As another example, plasma-based techniques such as those described above may first be used to functionalize a substrate surface, followed by removal of a portion of the functional groups at the surface by exposing the surface to a laser beam, for example, in an inert atmosphere (e.g., argon) so as to minimize the creation of new functional groups.

As another example, the substrate can be provided with a positive charge by covalently linking species with functional groups having positive charge (e.g., amine, imine or other basic groups) or functional groups having a negative charge (e.g., carboxylic, phosphonic, phosphoric, sulfuric, sulfonic, or other acid groups) using methods well known in the art.

Covalent linkage may proceed via a number of chemically reactive functional groups, including amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups, among others. Covalent coupling of charged species to surfaces, where the charged species and surface each have reactive functional groups, may be carried out, for example, by direct reaction between such functional groups, or more typically by using linking agents that contain reactive moieties capable of reaction with such functional groups. Specific examples of commonly used linking agents include glutaraldehyde, diisocyanates, diiosothiocyanates, bis(hydroxysuccinimide)esters, maleimidehydroxysuccinimide esters, carbodiimides, N,N'-carbonyldiimidazole imidoesters, and difluorobenzene derivatives, among others.

One ordinarily skilled in the art will recognize that any number of other coupling agents may be used depending on the functional groups present. In some embodiments, it may be desirable for the surface and the charged species to have differing functional groups, so as to avoid self-coupling reactions. Functional groups present on the charged species and/or surface may be converted, as desired, into other functional groups prior to reaction, e.g. to confer additional reactivity or selectivity. Further information on covalent coupling may be found, for example, in U.S. Pub. No. 2005/0002865.

As another example, charged groups may be introduced by non-covalently binding charged compounds to the polymers, for example, based on van der Waals interactions, hydrogen bonding, hydrophilic/hydrophobic interactions and/or other interactions between the substrate and the charged compounds.

For instance, a surface charge may be provided on a substrate by exposing the substrate to a charged amphiphilic substance. Amphiphilic substances include any substance having hydrophilic and hydrophobic groups. Where used, the amphiphilic substance should have at least one electrically charged group to provide the substrate surface with a net electrical charge. Therefore, the amphiphilic substances that are used herein can also be referred to as an ionic amphiphilic substances.

Amphiphilic polyelectrolytes are used as ionic amphiphilic substances in some embodiments.

In some embodiments, a surface charge is provided on a substrate by adsorbing polycations (for example, selected from polyethylenimine (PEI), protamine sulfate, polyallylamine, polydiallyldimethylammonium species, chitosan, gelatin, spermidine, and albumin, among others) or by adsorbing polyanions (for example, selected from polyacrylic acid, sodium alginate, polystyrene sulfonate (PSS), eudragit, gelatin, hyaluronic acid, carrageenan, chondroitin sulfate, and carboxymethylcellulose, among others) to the surface of the substrate as a first charged layer. PEI is commonly used for this purpose, as it strongly promotes adhesion to a variety of substrates. Although full coverage may not be obtained for the first layer, once several layers have been deposited, a full coverage should ultimately be obtained, and the influence of the substrate is expected to be negligible. The feasibility of this process has been demonstrated on glass substrates using charged polymeric (polyelectrolyte) materials. See, e.g., "Multilayer on solid planar substrates," *Multilayer thin films, sequential assembly of nanocomposite materials*, Wiley-VCH ISBN 3-527-30440-1, Chapter 14; and "Surface-chemistry technology for microfluidics," Hau, Winky L. W. et al. *J. Micromech. Microeng.* 13 (2003) 272-278.

Species for establishing a surface charge may be applied to the substrate by a variety of techniques. These techniques include, for example, full immersion techniques such as dipping techniques, spraying techniques, roll and brush coating techniques, techniques involving coating via mechanical suspension such as air suspension, ink jet techniques, spin coating techniques, web coating techniques and combinations of these processes, among others. Micro-polymer stamping may also be employed as described in S. Kidambi et al., "Selective Depositions on Polyelectrolyte Multilayers: Self-Assembled Monolayers of m-dPEG Acid as Molecular Templates" *J. Am. Chem. Soc.* 126, 4697-4703, 2004. The choice of the technique will depend on the requirements at hand. For example, full immersion techniques may be employed where it is desired to apply the species to an entire substrate, including surfaces that are hidden from view (e.g., surfaces which cannot be reached by line-of-sight techniques, such as spray techniques). On the other hand, spraying, roll coating, brush coating and ink jet printing may be employed, for instance, where it is desired to apply the species only certain portions of the substrate (e.g., in the form of a pattern).

Once a sufficient surface charge is provided on a substrate, it can be readily coated with a layer of an oppositely charged material. Examples of such layers include layers that contain one or more of the following charged species: (a) charged therapeutic agents, including therapeutic agents that comprise one or more polyelectrolyte blocks, (b) charged block copolymers, including block copolymers that comprise one or more polyelectrolyte blocks, (c) polyelectrolytes, that are neither charged therapeutic agents nor charged block copolymers, and (d) charged particles, including microparticles, nanoparticles, nanocapsules and micelles, which may optionally contain a therapeutic agent.

Multilayer regions are formed by repeated treatment with alternating, oppositely charged materials, i.e., by alternating treatment with materials that provide positive and negative surface charges. The layers self-assemble by means of electrostatic layer-by-layer deposition, thus forming a multilayered region over the substrate.

As noted above, in accordance with certain aspects of the present invention, at least one charged block copolymer is found within the charged layers of the devices of the present invention.

As used herein, "block copolymers" are copolymers that contain two or more differing polymer blocks, for instance, because a constitutional unit (i.e., monomer) is found in one polymer block that is not found in another polymer block. As used herein, a "polymer block" is a grouping of constitutional units (e.g., 5 to 10 to 25 to 50 to 100 to 250 to 500 to 1000 or more units) that forms part or all of a polymer. Blocks can be branched or unbranched. Blocks can contain a single type of constitutional unit (also referred to herein as "homopolymeric blocks") or multiple types of constitutional units (also referred to herein as "copolymeric blocks") which may be provided, for example, in a random, statistical, gradient, or periodic (e.g., alternating) distribution. As used herein, a "chain" is a linear (unbranched) grouping of constitutional units (i.e., a linear block).

Because they are formed from two or more differing polymer blocks, block copolymers frequently possess many interesting physical and chemical properties. Specific examples include polystyrene-polyisobutylene-polystyrene triblock copolymers (SIBS copolymers) as described above. Polyisobutylene has a low glass transition temperature ($T_g$) and is soft and elastomeric at room (and body) temperature, giving these copolymers elastomeric properties. Polystyrene, on the other hand, has a much higher $T_g$ and is thus hard at these temperatures, strengthening the copolymer. Depending upon the relative amounts of polystyrene and polyisobutylene, these copolymers can be formulated to have a range of hardness, for example, from as soft as about Shore 10A to as hard as about Shore 100D. Such block copolymers, however, are not charged to any significant degree and are therefore not amenable for use in layer-by-layer techniques.

Block copolymers for use in the charged layers of the devices of the present invention, on the other hand, are charged to a degree sufficient to allow them to participate in electrostatic assembly processes. Charged block copolymers for the practice of the invention may include at least one polyelectrolyte block (i.e., a polymer block having multiple charged sites, for example, a polyanionic block, which has an overall negative charge, or a polycationic block, which has an overall positive charge). As noted above, polymer blocks can be homopolymer blocks or copolymer blocks, and can be branched or unbranched, and the same applies to polyelectrolyte blocks. A wide variety of polyelectrolyte blocks may be employed within charged block copolymers for use in the practice of the invention, including polyelectrolyte blocks corresponding to the various polyelectrolytes described above.

In certain embodiments, the charged block copolymers for the practice of the invention may include one or more low $T_g$ blocks (which may or may not be polyelectrolyte blocks) and one or more high $T_g$ blocks (which may or may not be polyelectrolyte blocks). "Low $T_g$ polymer blocks" are polymer blocks that display a $T_g$ that is below body temperature (37° C.), typically 35° C. to 25° C. to 0° C. to −25° C. to −50° C. or less. Conversely, elevated or "high $T_g$ polymer blocks" are polymer blocks that display a glass transition temperature that is above body temperature, typically 40° C. to 50° C. to 75° C. to 100° C. to 125° C. or more. Low $T_g$ polymer chains are generally soft and elastomeric at body temperature, whereas high $T_g$ polymer chains are generally hard at body temperature. $T_g$ can be measured by any of a number of techniques including differential scanning calorimetry (DSC).

A few examples of charged block copolymers that contain two types of polymer blocks, A and B, at least one of which is a polyelectrolyte block, follow. Examples include block copolymers having the following structures: (a) $AB_n$ or $BA_n$, where n is an integer, for example, AB (diblock) where n=1, ABA or BAB (triblock copolymers) where n=2, $AB_3$ or $BA_3$ (three-arm, star-shaped copolymers) where n=3, and so forth. Other examples include alternating configurations such as $(AB)_n$, $B(AB)_n$, $(BA)_n$ or $A(BA)_n$. Note that it is common to disregard the presence of small entities X (e.g., seed molecules, linking groups, etc.) in describing block copolymers, for example, with BA-X-AB being commonly designated as a triblock copolymer BAB. Further examples of block copolymers include those that contain a main chain A and numerous side chains B or, conversely, a main chain B and numerous side chains A.

In certain beneficial embodiments, the A polymer blocks in the prior paragraph are low $T_g$ blocks, and the B polymer blocks are high $T_g$ blocks, wherein the A blocks, the B blocks, or both the A blocks and the B blocks, may be polyelectrolyte blocks.

Certain specific embodiments utilize charged copolymers that comprise one or more polyolefin blocks and one or more charged poly(vinyl aromatic blocks), including linear and branched (e.g., multi-arm, comb, dendritic, etc.) copolymers.

Such polymers may be functionalized anionic groups, such as sulfonate or carboxylate groups, or cationic groups, such as ammonium groups. Specific examples of such polymers include block copolymers having sulfonated poly(vinyl aromatic) and polyolefin blocks, for example, sulfonated polystyrene-polyolefin-polystyrene triblock copolymers such as the sulfonated polystyrene-poly(ethylene/butylene)-polystyrene triblock copolymers described in U.S. Pat. No. 5,840,387, and sulfonated versions of the polystyrene-polyisobutylene-polystyrene (SIBS) triblock copolymers described in U.S. Pat. No. 6,545,097 to Pinchuk et al., which polymers may be sulfonated, for example, using the processes described in U.S. Pat. No. 5,840,387 and U.S. Pat. No. 5,468,574, among other sufonated block copolymers. Polymers of this type are also described in Elabd and Napadensky, "Sulfonation and Characterization of Poly(styrene-isobutylene-styrene) Triblock Copolymers at High Ion-Exchange Capacities," *Polymer* 45 (2004) 3037-3043; Elabd et al., *Journal of Membrane Sci.*, 217 (2003) 227; Blackwell and Mauritz, *Polymer* 45 (2004) 3457, Storey and Baugh, *Polymer* 42 (2001) 2321; Edmonson and Fontanella, *Solid State Ionics* 152-153 (2002) 355; and Kwon and Puskas, *European Polymer Journal* 40 (2004) 119.

Specific examples of such polymers further include block copolymers having amine-modified-poly(vinyl aromatic) and polyolefin blocks, for example amine-modified polystyrene-polyolefin-polystyrene triblock copolymers such as polyaniline-poly(ethylene/butylene)-polyaniline triblock copolymers or polyaniline-polyisobutylene-polyaniline triblock copolymers. Such block copolymers may be formed by a variety of techniques such as sequential polymerization or by covalently linking monofunctionalized polyaniline to difunctionalized polyolefin via any of a number of covalent linking schemes such as those described above, among others. Such block copolymers may also be provided in alternating layers or complexed with their sulfonated family members (see prior paragraph) if desired. See, e.g., M.-K. Park et al., *Langmuir,* 19, 8550-8554 (2003). "Self-assembly and characterization of polyaniline and sulfonated polystyrene multilayer-coated colloidal particles and hollow shells." and I. Y. Sakharov et al., "Modeling and characterization of polyelectrolyte complex of polyaniline and sulfonated polystyrene produced by palm tree peroxidase," *Synthetic Metals* 142 (2004) 127-135.

As noted above, charged layers in accordance with the present invention may also include at least one charged therapeutic agent.

By "charged therapeutic agent" is meant a therapeutic agent that has an associated charge. For example, a therapeutic agent may have an associated charge because it is inherently charged (e.g., because it has acidic and/or or basic groups, which may be in salt form). A few examples of inherently charged cationic therapeutic agents include amiloride, digoxin, morphine, procainamide, and quinine, among many others. Examples of anionic therapeutic agents include heparin and DNA, among many others.

A therapeutic agent may have an associated charge because it has been chemically modified to provide it with one or more charged functional groups.

For instance, conjugation of water insoluble or poorly soluble drugs, including anti-tumor agents such as paclitaxel, to hydrophilic polymers has recently been carried out in order to solubilize the drug (and in some cases to improve tumor targeting and reduce drug toxicity). Similarly cationic or anionic versions of water insoluble or poorly soluble drugs have also been developed.

Taking paclitaxel as a specific example, various cationic forms of this drug are known, including paclitaxel N-methyl pyridinium mesylate and paclitaxel conjugated with N-2-hydroxypropyl methyl amide, as are various anionic forms of paclitaxel, including paclitaxel-poly(l-glutamic acid), paclitaxel-poly(l-glutamic acid)-PEO. See, e.g., U.S. Pat. No. 6,730,699; Duncan et al., *Journal of Controlled Release* 74 (2001)135; Duncan, *Nature Reviews/Drug Discovery*, Vol. 2, May 2003, 347; Jaber G. Qasem et al, *AAPS PharmSciTech* 2 003,4(2) Article 21. In addition to these, U.S. Pat. No. 6,730,699, also describes paclitaxel conjugated to various other charged polymers (e.g., polyelectrolytes) including poly(d-glutamic acid), poly(dl-glutamic acid), poly(l-aspartic acid), poly(d-aspartic acid), poly(dl-aspartic acid), poly(l-lysine), poly(d-lysine), poly(dl-lysine), copolymers of the above listed polyamino acids with polyethylene glycol (e.g., paclitaxel-poly(l-glutamic acid)-PEO), as well as poly(2-hydroxyethyl l-glutamine), chitosan, carboxymethyl dextran, hyaluronic acid, human serum albumin and alginic acid. Still other forms of paclitaxel include carboxylated forms such as 1'-malyl paclitaxel sodium salt (see, e.g. E. W. DAmen et al., "Paclitaxel esters of malic acid as prodrugs with improved water solubility," *Bioorg Med Chem.,* 2000 Feb., 8(2), pp. 427-32).

Polyglutamate paclitaxel, in which paclitaxel is linked through the hydroxyl at the 2' position to the Δ carboxylic acid of the poly-L-glutamic acid (PGA), is produced by Cell Therapeutics, Inc., Seattle, Wash., USA. (The 7 position hydroxyl is also available for esterification.) This molecule is said to be cleaved in vivo by cathepsin B to liberate diglutamyl paclitaxel. In this molecule, the paclitaxel is bound to some of the carboxyl groups along the backbone of the polymer, leading to multiple paclitaxel units per molecule. For further information, see, e.g., R. Duncan et al., "Polymer-drug conjugates, PDEPT and PELT: basic principles for design and transfer from the laboratory to clinic," *Journal of Controlled Release* 74 (2001) 135-146, C. Li, "Poly(L-glutamic acid)-anticancer drug conjugates," *Advanced Drug Delivery Reviews* 54 (2002) 695-713; Duncan, *Nature Reviews/Drug Discovery*, Vol. 2, May 2003, 347; Qasem et al, *AAPS PharmSciTech* 2003, 4(2) Article 21; and U.S. Pat. No. 5,614,549.

Using the above and other strategies, paclitaxel and many other therapeutic agents may be covalently linked or otherwise associated with a variety of charged species, including charged polymer molecules (e.g., polyelectrolytes), thereby forming charged drugs and prodrugs.

A therapeutic agent may also have an associated charge because it is attached to a charged particle, for example, attached to a charged nanoparticle (i.e., a charged particle having a cross-sectional dimension of 100 nm or less, for example, a spherical particle or a rod-shaped particle having a diameter of 100 nm or less) or because it is encapsulated within a charged particle, for example, encapsulated within a charged nanocapsule or within a charged micelle, among others.

The therapeutic agent may be provided within a charged capsule, for example, using layer-by-layer techniques in which capsules are formed from alternating layers of polyanions and polycations such as those described above and in commonly assigned U.S. Ser. No. 10/768,388 , entitled "Localized Drug Delivery Using Drug-Loaded Nanocapsules." For a specific example of such a technique, see I. L. Radtchenko et al., "A novel method for encapsulation of poorly water-soluble drugs: precipitation in polyelectrolyte multilayer shells," *International Journal of Pharmaceutics,* 242 (2002) 219-223.

Using the above and other techniques, a wide range of therapeutic agents may be provided with associated charges.

"Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be themselves pharmaceutically active, or they may converted in vivo into pharmaceutically active substances (e.g., they may be prodrugs).

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.), among others.

Further exemplary non-genetic therapeutic agents, not necessarily exclusive of those listed above, include paclitaxel (including particulate forms thereof, for instance, protein-bound paclitaxel particles such as albumin-bound paclitaxel nanoparticles, e.g., ABRAXANE®), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17 , abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2 , BMP-3 , BMP-4 , BMP-5 , BMP-6 (Vgr-1), BMP-7 (OP-1), BMP-8 , BMP-9 , BMP-10, BMP-11 , BMP-12 , BMP-13 , BMP-14 , BMP-15 , and BMP-16 . Currently preferred BMP's are any of BMP-2 , BMP-3 , BMP-4 , BMP-5 , BMP-6 and BMP-7 . These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (by Supratek Pharms Inc.), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Hence, agents useful for the practice of the present invention may be selected from the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, () platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings may be used in the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the medical device including the nature of its multilayer region(s), and so forth.

Therapeutic agent loading may be varied, for example, by varying the number of the charged layers containing the therapeutic agent(s), by varying the amount of therapeutic agent(s) in each layer (e.g., by combining the charged therapeutic agent with another charged compound, such as a charged block copolymer or another polyelectrolyte described elsewhere herein, thereby decreasing the amount of therapeutic agent that is deposited), and so forth.

The therapeutic agent release profile may also be varied, for example, by varying the number of the charged layers containing the therapeutic agent(s) and by varying the amount of therapeutic agent(s) in each layer, as well as by varying the position of the therapeutic agent containing layers within the multiple charged layers (with therapeutic agents in deeper layers being expected to take longer to be released than therapeutic agents in layers that are nearer the surface, whether release is due to diffusion through overlying layers, due to breakdown of the charged layer structure in vivo, etc.).

The therapeutic agent release profile may also be varied, for example, by creating covalent bonds between and/or within the charged layers, for example, by promoting crosslinking reactions (e.g., through the application of heat, the use of crosslinking agents, etc.), which will decrease the release kinetics.

Layer-by-layer assembly may be conducted, for example, by sequentially exposing a selected charged substrate to solutions or suspensions that contain species of alternating net charge, including solutions or suspensions that contain one or more of the following charged species: (a) charged therapeutic agents, including therapeutic agents that comprise one or more polyelectrolyte blocks, (b) charged block copolymers, including block copolymers that comprise one or more polyelectrolyte blocks, (c) polyelectrolytes, which are neither charged therapeutic agents nor charged block copolymers, and (d) charged particles, including microparticles, nanoparticles, nanocapsules and micelles, which may optionally contain a therapeutic agent.

The concentration of the charged species within these solutions and suspensions can vary widely, with typical values being on the order of from 0.01 to 10 mg/ml.

Moreover the pH of these solutions and suspensions may be set as desired. Buffer systems may be employed for this purpose, if needed. The charged entities chosen may be ionized at neutral pH (e.g., at pH 6-8) or at the pH of the body location where the device is to be inserted or implanted, among other possibilities.

Moreover, the addition of salt (e.g., NaCl, KCl, etc.) to the solution or suspension is known to have an effect on the composition of the coating. For example, the higher the salt concentration, the less electrostatic bonds are made between two adjacent layers. Consequently a more open structure is formed. This may result, for example, in a higher rate of release of therapeutic agent.

The solutions and suspensions containing the charged species may be applied to the charged substrate surface using a variety of techniques including, for example, full immersion techniques such as dipping techniques, spraying techniques, roll and brush coating techniques, techniques involving coating via mechanical suspension such as air suspension, ink jet techniques, spin coating techniques, web coating techniques, polymer stamping, and combinations of these processes. As noted above, the choice of the technique will depend on the requirements at hand, with full immersion techniques being employed, for instance, where it is desired to apply the species to an entire substrate (including surfaces that are hidden from view) and spraying, roll coating, brush coating, ink jet printing, polymer stamping, and so forth being employed, for instance, where it is desired to apply the species only certain portions of the substrate. As a specific example, medical devices (e.g., tubular implants, such as stents and grafts) may be produced in which only the solid tissue contacting areas (e.g., the outer surface of the stent or the inner surface of the graft) are provided with a therapeutic agent containing multilayer region.

In various embodiments, the substrate is rinsed after application of each charged species layer, to remove unbound material.

Using these and other techniques, multiple layers of alternating charge may be applied over the underlying substrate, selected, for example, from layers containing one or more of the following, among others: (a) charged therapeutic agents, including therapeutic agents that comprise one or more polyelectrolyte blocks, (b) charged block copolymers, including block copolymers that comprise one or more polyelectrolyte blocks, (c) polyelectrolytes that are neither charged therapeutic agents nor charged block copolymers, and (d) charged particles, including microparticles, nanoparticles, nanocapsules and micelles, which may optionally contain a therapeutic agent. In some embodiments, between 10 and 200 (e.g., from 10 to 25 to 50 to 100 to 200) layers are applied over the substrate. The total thickness of the multilayer region that is assembled may vary widely, typically ranging, for example, from 10 nanometers to 40 micrometers (microns), more typically from 100 nanometers to 10 microns.

In some embodiments, a charged block copolymer and a charged therapeutic agent may be provided in the same layer, in which case they may be of the same charge. In some embodiments, the charged block copolymer and the charged therapeutic agent may be provided in separate layers, in which case they may be of the same charge (e.g., both positive or both negative) or different charge (e.g., one positive, one negative).

In some embodiments, multiple charged layers may be provided, which include (a) one or more positively charged layers that contain a positively charged block copolymer, (b) one or more negatively charged layers that contain a negatively charged block copolymer, or both (a) and (b).

In some embodiments, multiple charged layers may be provided, which include (a) one or more positively charged layers that contain a positively charged therapeutic agent, (b) one or more negatively charged layers that contain a negatively charged therapeutic agent, or both (a) and (b).

In some embodiments charged layers may be provided which include polyelectrolytes (e.g., polyanions or polycations) that are neither therapeutic agents nor block copolymers.

In some embodiments charged layers may be provided which include charged particles.

One or more charged species may be found within a given layer including the following: (a) charged therapeutic agents, including therapeutic agents that comprise one or more polyelectrolyte blocks, (b) charged block copolymers, including block copolymers that comprise one or more polyelectrolyte blocks, (c) polyelectrolytes that are neither charged therapeutic agents nor charged block copolymers, and (d) charged particles, including microparticles, nanoparticles, nanocapsules and micelles, which may optionally contain a therapeutic agent, as well as any combination of the same, for example, combinations of (a) and (b), combinations of (a) and (c), combinations of (a) and (d), combinations of (b) and (c), combinations of (b) and (d), combinations of (c) and (d), combinations of (a), (b) and (c), and so forth.

A variety of outer top layers may be provided for the multilayer regions of the present invention. For instance, in some embodiments, the outer top layer contains containing one or more of the following, among others: (a) charged therapeutic agents, including therapeutic agents that comprise one or more polyelectrolyte blocks, (b) charged block copolymers, including block copolymers that comprise one or more polyelectrolyte blocks, (c) polyelectrolytes that are neither charged therapeutic agents nor charged block copolymers, and (d) charged particles, including microparticles, nanoparticles, nanocapsules and micelles, which may optionally contain a therapeutic agent.

Several six-layer schemes are presented in Tables 1 and 2 below to illustrate just a few ways in which various layers may be arranged, specifically (a) layers containing charged block copolymers, such as anionic or cationic SIBS, among many others including those described above (designated "Copoly+" or "Copoly−" depending on the charge of the layer) (b) layers containing charged therapeutic agent, such as paclitaxel conjugated to a polycation or polyanion, among many others including those described above (designated "Drug+" or "Drug−" depending on the charge of the layer), and (c) layers containing cationic or anionic polyelectrolytes that are neither therapeutic agents nor block copolymers, such as PEI, PAH, polylysine, polyglutamate, among many others including those described above (designated "Poly+" or "Poly−" depending on the charge of the layer).

TABLE 1

|         | Ex. 1   | Ex. 2   | Ex. 3   | Ex. 4   | Ex. 5            | Ex. 6            | Ex. 7            |
|---------|---------|---------|---------|---------|------------------|------------------|------------------|
| Layer F | Drug+   | Drug−   | Copoly− | Copoly− | Copoly−<br>Drug− | Copoly−          | Copoly−<br>Drug− |
| Layer E | Copoly− | Copoly+ | Copoly+ | Copoly+ | Copoly+          | Copoly+<br>Drug+ | Copoly+<br>Drug+ |
| Layer D | Drug+   | Drug−   | Drug−   | Copoly− | Copoly−<br>Drug− | Copoly−          | Copoly−<br>Drug− |
| Layer C | Copoly− | Copoly+ | Copoly+ | Drug+   | Copoly+          | Copoly+<br>Drug+ | Copoly+<br>Drug+ |
| Layer B | Drug+   | Drug−   | Copoly− | Copoly− | Copoly−<br>Drug− | Copoly−          | Copoly−<br>Drug− |
| Layer A | Copoly− | Copoly+ | Copoly+ | Copoly+ | Copoly+          | Copoly+<br>Drug+ | Copoly+<br>Drug+ |

TABLE 2

|         | Ex. 8   | Ex. 9   | Ex. 10  | Ex. 11  | Ex. 12           | Ex. 13           | Ex. 14           |
|---------|---------|---------|---------|---------|------------------|------------------|------------------|
| Layer F | Poly−   | Poly+   | Poly−   | Poly−   | Copoly−<br>Drug− | Copoly−          | Poly−<br>Drug−   |
| Layer E | Copoly+ | Copoly− | Drug+   | Copoly+ | Poly+            | Poly+<br>Drug+   | Copoly+<br>Drug+ |
| Layer D | Drug−   | Drug+   | Poly−   | Drug−   | Copoly−<br>Drug− | Copoly−<br>Drug− | Poly−<br>Drug−   |
| Layer C | Copoly+ | Copoly− | Copoly+ | Copoly+ | Poly+            | Poly+            | Copoly+<br>Drug+ |
| Layer B | Poly−   | Poly+   | Poly−   | Poly−   | Copoly−          | Copoly−          | Poly−<br>Drug−   |
| Layer A | Copoly+ | Copoly− | Copoly+ | Copoly+ | Poly+            | Poly+            | Copoly+<br>Drug+ |

In this regard, Examples 1 and 2 illustrate alternation between layers that contain a therapeutic agent and layers that contain a block copolymer of opposite charge, Examples 3 and 4 illustrate alternation between layers that contain block copolymers of opposite charge, in which a layer that contains a therapeutic agent is substituted for one of the block copolymer layers, Examples 5 and 6 illustrate alternation between layers that contain block copolymer and therapeutic agent and layers of opposite charged that contain only block copolymer, Example 7 illustrates alternation between layers of opposite charge that contain both block copolymer and therapeutic agent, Examples 8 and 9 illustrate alternation between layers that contain block copolymer, layers that contain polyelectrolyte, and layers that contain therapeutic agent, Example 10 illustrates alternation between layers that contain block copolymer and layers that contain polyelectrolyte in which a layer that contains a therapeutic agent is substituted for one of the block copolymer layers, Example 11 illustrates alternation between layers that contain block copolymer and layers that contain polyelectrolyte in which a layer that contains a therapeutic agent is substituted for one of the polyelectrolyte layers, Example 12 illustrates alternation between layers that contain block copolymer and layers that contain polyelectrolyte in which a therapeutic agent added to two of the block copolymer layers, Example 13 illustrates alternation between layers that contain block copolymer and layers that contain polyelectrolyte in which a therapeutic agent is added to one of the polyelectrolyte layers, and Example 14 illustrates alternation between layers that contain block copolymer and layers that contain polyelectrolyte in which a therapeutic agent is added to the block copolymer layers and to the polyelectrolyte layers.

Clearly the variations are essentially endless.

Figure 1B:
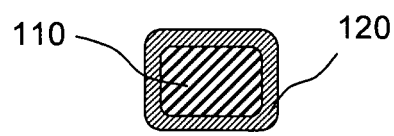
FIG. 1B is schematic view of a cross section taken along line b-b of FIG. 1A.

Further specific embodiments of the invention will now be described with reference to the Figures. Referring now to FIGS. 1A and 1B, a stent 100 is shown, in accordance with an embodiment of the present invention. As seen from FIG. 1B, which is a cross section taken along line b-b of FIG. 1A, the stent 100 comprises a substrate 110, which may be, for example, a metallic substrate such as a nitinol or stainless steel substrate or a bioresorbable metal substrate such as iron, magnesium or their alloys, among others. Disposed over the substrate is a multilayer region 120 in accordance with the present invention, which as noted above contains multiple charged layers of alternating charge, which may be applied, for example, as previously discussed. The multiple charged layers, in turn, include (i) at least one charged block copolymer and (ii) at least one charged therapeutic agent.

EXAMPLE

A stainless steel, Express® stent (Boston Scientific Inc., Natick, Mass., USA) is pretreated with oxidation by immersion in a $H_2O_2/NH_3$ solution.

A first primer layer consisting of high molecular weight Chitosan (Aldrich, Inc., Cat No. 41,941-9) made in a solution of 1.5 mg/mL in 0.1 M acetic acid containing 0.14 M NaCl, pH 4 is deposited on the surface by a 5 minute immersion step. Ultrapure water (18.2 MOhm/cm²) (Milli Q system, Millipore, Inc.) is used for washing in between all adsorption steps.

Sulfonated SIBS may be prepared in accordance with the procedures set forth in Yossef A. Elabd and Eugene Napadensky, "Sulfonation and characterization of poly(styrene-isobutylene-styrene) triblock copolymers at high ion-exchange capacities," *Polymer* 45 (2004) 3037-3043 . Paclitaxel-poly (l-glutamic acid) may be obtained under the name XYOTAX® from Cell Therapeutics, Inc., Seattle, Wash., USA. An aqueous solution containing 1 mg/ml of XYOTAX® (MW 48000 Dalton), in 0.1 M sodium acetate/0.1M acetic acid buffer pH=5.4 may be prepared. The solution may be adjusted for an appropriate balance with polycations, such as chitosan or poly-lysine. Similarly, an aqueous solution containing 1 mg/ml sulfonated SIBS, pH 3.0, may be prepared, also adjusting the solution for an appropriate balance with polyanions, such as polyglutamate, as needed.

20 alternating layers of (a) cationic Chitosan and (b) anionic paclitaxel-poly(l-glutamic acid) or anionic sulfonated SIBS (e.g., alternating between anionic layers of paclitaxel-poly[l-glutamic acid] and sulfonated SIBS) are deposited by repeated immersion and rinsing steps, using solutions such as those described above.

A solution of 1 g/L heparin sodium salt, (Alfa Aesar A16198) in 0.1 M NaCl buffered with 0.05 M sodium acetate at pH 6.2 is prepared and a final 10 layers of alternating Heparin and Chitosan are adsorbed on the surface by repeated immersion and rinsing steps.

Although various embodiments of the invention are specifically illustrated and described herein, it will be appreciated that modifications and variations of the present invention are covered by the above teachings without departing from the spirit and intended scope of the invention.

The invention claimed is:

1. A medical device comprising: (a) a substrate; (b) a multilayer region comprising multiple charged layers of alternating charge deposited by layer-by-layer electrostatic self-assembly over said substrate, said multiple charged layers comprising (i) a plurality of first charged layers that comprise a charged block copolymer that comprises a polyelectrolyte block, wherein said block copolymer comprises a polyisobutylene block and a charged poly(vinyl aromatic) block selected from sulfonated poly(vinyl aromatic) blocks and amine-modified-poly(vinyl aromatic) blocks, and (ii) a plurality of second charged layers that comprise a charged therapeutic agent that comprises a covalently linked polyelectrolyte block, wherein said medical device is configured for implantation or insertion into a patient, with the proviso that said medical device does not comprise two or more electrodes, wherein said charged therapeutic agent is a paclitaxel prodrug, wherein said charged therapeutic agent comprises a covalently linked charged poly(amino acid) portion, wherein said plurality of first charged layers comprise a plurality of positively charged layers that comprise a positively charged block copolymer which comprises said amine-modified-poly(vinyl aromatic) block and said polyisobutylene block, wherein said plurality of first charged layers comprise a plurality of negatively charged layers that comprise a negatively charged block copolymer which comprises said sulfonated poly(vinyl aromatic) block and said polyisobutylene block, wherein said multilayer region has a total thickness of between 10 nanometers 40 microns.

2. The medical device of claim 1, wherein said multilayer region comprises at least 10 of said charged layers of alternating charge.

3. The medical device of claim 1, wherein said multilayer region comprises at least 25 of said charged layers of alternating charge.

4. The medical device of claim 1, wherein said first and second charged layers are of opposite charge.

5. The medical device of claim 1, wherein said first and second charged layers are of the same charge.

6. The medical device of claim 1, wherein said charged block copolymer comprises a plurality of said polyelectrolyte blocks.

7. A medical device comprising: (a) a substrate; (b) a multilayer region comprising multiple charged layers of alternating charge deposited by layer-by-lager electrostatic self-assembly over said substrate, said multiple charged layers comprising (i) a plurality of first charged layers that comprise a charged block copolymer that comprises a polyelectrolyte block, wherein said block copolymer comprises a polyisobutylene block and a charged poly(vinyl aromatic) block selected from sulfonated poly(vinyl aromatic) blocks and amine-modified-poly(vinyl aromatic) blocks, and (ii) a plurality of second charged layers that comprise a charged therapeutic agent that comprises a covalently linked polyelectrolyte block, wherein said medical device is configured for implantation or insertion into a patient, with the proviso that said medical device does not comprise two or more electrodes, wherein said charged therapeutic agent comprises a covalently linked charged poly(amino acid) portion, wherein said charged therapeutic agent is a paclitaxel prodrug, wherein said block copolymer comprises said polyisobutylene block as a center block and a plurality of said sulfonated poly(vinyl aromatic) blocks as end blocks, wherein said multilayer region has a total thickness of between 10 nanometers 40 microns.

8. The medical device of claim 1, wherein said block copolymer comprises said amine-modified poly(vinyl aromatic) block and said polyisobutylene block.

9. The medical device of claim 1, wherein said charged therapeutic agent comprises a polycationic block.

10. The medical device of claim 1, wherein said charged therapeutic agent comprises a polyanionic block.

11. The medical device of claim 1, wherein said poly(amino acid) portion is selected from a polyglutamate portion, a polyaspartate portion, a polylysine portion, a polyarginine portion and a polyornithine portion.

12. The medical device of claim 1, wherein said plurality of second charged layers comprise a plurality of positively charged layers that comprise a positively charged therapeutic agent.

13. The medical device of claim 1, wherein said plurality of second charged layers comprise a plurality of negatively charged layers that comprise a negatively charged therapeutic agent.

14. The medical device of claim 1, wherein said medical device comprises a plurality of therapeutic agents.

15. The medical device of claim 1, wherein said multilayer region is bioerodable.

16. The medical device of claim 1, wherein said medical device comprises a plurality of distinct multilayer regions.

17. The medical device of claim 1, wherein said medical device is selected from a balloon catheter, a guidewire, a stent, a graft, and a filter.

18. The medical device of claim 1, further comprising a plurality of third charged layers that comprise a polyelectrolyte that is neither a block copolymer nor a therapeutic agent.

19. The medical device of claim 1, wherein said multilayer region comprises charged particles.

20. The medical device of claim 1, wherein said charged particles comprise a therapeutic agent.

21. The medical device of claim 1, further comprising a third charged layer that comprises a polyelectrolyte that is neither a block copolymer nor a therapeutic agent.

22. The medical device of claim 1, further comprising a third charged layer that comprises chitosan.

23. The medical device of claim 1, further comprising a third charged layer that comprises a proteoglycan.

24. The medical device of claim 1, wherein said medical device is a stent.

25. A stent comprising: (a) a substrate; (b) a multilayer region comprising at least 10 layers of alternating charge deposited by layer-by-layer electrostatic self-assembly over said substrate, said multiple charged layers comprising (i) a plurality of first charged layers that comprise a charged sulfonated polystyrene-polyolefin-polystyrene triblock copolymer, an amine-modified polystyrene-polyolefin-polystyrene triblock copolymer, or a combination thereof, (ii) a plurality of second charged layers that comprise a charged therapeutic agent that comprises a covalently linked charged poly(amino acid) portion and (iii) a plurality of third charged layers that comprise a polycationic polysaccharide that is neither a block copolymer nor a therapeutic agent, with the proviso that said stent does not comprise two or more electrodes, the multilayer region having a total thickness of between 10 nanometers 40 microns.

26. The medical device of claim 25, wherein said charged therapeutic agent is an anti-restenosis agent.

27. The medical device of claim 1, wherein said charged block copolymer comprises a polyisobutylene block and a polystyrene sulfonate block, and wherein said charged therapeutic agent comprises a covalently linked charged poly (amino acid) portion.

28. The medical device of claim 27, wherein said therapeutic agent is an antiproliferative agent.

* * * * *